United States Patent [19]

Hölzel et al.

[11] Patent Number: 4,971,784

[45] Date of Patent: Nov. 20, 1990

[54] PRESERVED HAIR-AND BODY-CLEANING AGENT AND THE USE OF A PRESERVATIVE COMBINATION

[75] Inventors: Hans Hölzel, Fränkisch-Crumbach; Eugen Konrad, Darmstadt; Horst Schwarz, Fliederweg, all of Fed. Rep. of Germany

[73] Assignee: Wella Aktiengesellschaft, Darmstadt, Fed. Rep. of Germany

[21] Appl. No.: 272,752

[22] PCT Filed: Mar. 15, 1988

[86] PCT No.: PCT/EP88/00200

§ 371 Date: Oct. 6, 1988

§ 102(e) Date: Oct. 6, 1988

[87] PCT Pub. No.: WO88/08293

PCT Pub. Date: Nov. 3, 1988

[30] Foreign Application Priority Data

Apr. 24, 1987 [DE] Fed. Rep. of Germany ....... 3713684

[51] Int. Cl.$^5$ ............................................. A61K 7/075

[52] U.S. Cl. ...................................... 424/70; 514/578; 514/784; 514/568; 514/544; 424/605

[58] Field of Search .................. 424/70, 605; 514/557, 514/568, 576, 578, 784, 544

[56] References Cited

PUBLICATIONS

Decker, Jr. "Frequency of Preservative Use in Cosmetic Formulas as Disclosed to FDA–1984" Cosmetics & Toiletries vol. 100 Feb. 1985, pp. 65–68.
Cosmetics and Toiletries vol. 100 p. 97 1985 (Feb.).

*Primary Examiner*—Merrell C. Cashion, Jr.
*Assistant Examiner*—Susan S. Rucker
*Attorney, Agent, or Firm*—Michael J. Striker

[57] ABSTRACT

The hair- and body-cleaning agent contains a combination of (A) a physiologically compatible salt of formic acid, (B) benzoic acid or its physiologically compatible salt and (C) a physiologically harmless inorgnic or aliphatic organic acid as well as a surfactant or surfactant mixture. This hair- and body-cleaning agent is very well preserved and also very well compatible.

22 Claims, No Drawings

PRESERVED HAIR-AND BODY-CLEANING AGENT AND THE USE OF A PRESERVATIVE COMBINATION

The present invention relates to a preserved hair- and body-cleaning composition and method for preserving a hair and body-cleaning composition.

THE BACKGROUND OF THE INVENTION

Hair- and body-cleaning agents usually contain a preservative for effective protection of the agent against an attack by microorganisms.

A preservative for hair- and body-cleaning compositions must satisfy conflicting requirements. The preservative should be well compatible physiologically and dermatologically on the one hand and should have a germ-inhibiting or even germicidal effect on the other. However, these two requirements are usually difficult to combine with each other.

For example, the following conventional preservatives are commonly used in hair- and body-cleaning compositions: formaldehyde, 5-bromo-5-nitro-1,3-dioxane, p-hydroxy-benzoic ester, 2,4,4'-trichloro-2'-hydroxy-diphenyl ether, 5-chloro-2-methyl-3-isothiazolone, 2-methyl-3-isothiazolone, and 2-bromo-2-nitropropane-1,3-diol.

Recently a number of preservatives, as for example, formaldehyde and 2-methyl-3-isothiazolone, have been suspected of not being sufficiently compatible. It is known that aldehydes and phenols, which have a preserving effect, react with proteins and interact with them in a denaturating manner. In the case of aldehydes there additionally exists the risk of sensitization.

In the literature formic acid and benzoic acid have been described as preservatives. However, formic acid was not used in hair- and body-cleaning compositions heretofore and benzoic acid alone shows no adequate preserving effect in low concentrations while it has an undesired keratolytic effect when applied in high concentrations. Formic acid has an unpleasantly pungent odor and an intensely corrosive effect. A further reason why formic acid is not applied as a preservative in hair- and body-cleaning compositions is that it has a low pH value at which there occurs a hydrolysis of the alkyl ether sulphates conventionally applied as surfactants in hair- and body care compositions.

SUMMARY OF THE INVENTION

Therefore, it is an object of the present invention to provide a hair- and body-cleaning composition containing a combination of preservatives having a good preserving effect and a better physiological and dermatological compatibility than conventional preservatives used in this type of composition.

In keeping with this object and with others which will become apparent hereinafter, the improved aqueous hair- and body-cleaning composition contains 3 to 50% by weight of a surfactant or surfactant mixture, which contains a combination of (A) a physiologically compatible salt of formic acid, (B) benzoic acid or its physiologically compatible salt, and (C) a physiologically harmless inorganic or aliphatic organic acid. If achieves this in an excellent manner.

The composition according to the present invention is very well preserved by the above-described combination of preservatives and has a very good compatibility.

The quality of the preservatives of the above-described hair- and body-cleaning compositions was determined by the preservation load test described in the literature (see The United States Pharmacopela, 21$^{st}$ Edition (1985), Page 1151). In this test the hair treatment compositions were polluted with the microorganisms Candida albicans (ATCC No. 10231), Aspergillus niger (ATCC No. 16404), Escherichia coli (ATCC No. 8739), Pseudomonas aeruginosa (ATCC No. 9027) and Staphylococcus aureus (ATCC No. 6538) and the development of the bacterial count was kept under observation for a period of 28 days.

While the use of sodium formate or benzoic acid—each time alone—particularly in the case of infestation by fungi, as for example, Aspergillus niger, does not result in a satisfactory preservation of the hair- and body-cleaning compositions, these compositions are very well preserved by the use of the above-described combination of the preservatives (A), (B) and (C), even against an attack by fungi.

Suitable physiologically compatible salts of formic acid (A) are, for example, sodium formate, ammonium formate, potassium formate and magnesium formate, sodium formate being preferred.

In the hair- and body-cleaning composition the component (A) is contained in an amount of approximately 0.01 to 2% by weight, preferably 0.1 to 1.0% by weight.

The composition according to the present invention contains the component (B) in an amount of approximately 0.05 to 2% by weight, preferably 0.1 to 1.0% by weight, primarily an alkali metal benzoate or the ammonium benzoate, particularly the sodium benzoate being suitable as salt of benzoic acid.

Preferred physiologically harmless aliphatic organic acids of the component (C) are aliphatic organic acids that are free from amino or halogen substituents and contain 2 to 6 carbon atoms, as for example, citric acid, tartaric acid, lactic acid, adipic acid, maleic acid, glyoxylic acid, gluconic acid and maleic acid, citric acid being preferred, while phosphoric acid is preferably used as inorganic acid of the component (C).

The component (C) is contained in the novel compositions in an amount of approximately 0.1 to 1.5% by weight, preferably in an amount of approximately 0.25 to 0.5% by weight.

The pH value of the hair- and body-cleaning compositions, which is 2.0 to 7.0, preferably 4.8 to 5.8, is adjusted with the component (C).

The hair- and body-cleaning composition according to the present invention is preferably in the form of an aqueous solution or emulsion and, apart from the combination of (A), (B) and (C), it contains at least one anionic, cationic and non-ionic or amphoteric surfactant in an amount of approximately 3 to 50% by weight, preferably 10 to 25% by weight.

Among the surfactants suitable for the novel hair- and body-treatment composition the following surfactants are mentioned here as examples:

(a) The anionic surface-active compositions, as for example, the alkali, alkaline earth, ammonium or alkanol-amine salts of alkane sulphonates, alkyl sulphates and alkyl ether sulphates, the $C_{12}$ to $C_{18}$- and particularly the $C_{12}$ to $C_{14}$-alkyl-sulphate sodium salts or alkyl-triethanolamine salts, the sodium or triethanol amine salts of lauryl or tetradecyl ether sulphates, the disodium salt of the sulphosuccinic semiester of alkanol amides, the soaps and the polyether carboxylic acids;

(b) the non-ionic surface-active agents, as for example, oxethylated fat alcohols containing 12 to 18 carbon atoms, for example, containing up to 40 moles of ethylene oxide per mole of fat alcohol, oxethylated lauryl tetradecyl, cetyl, oleyl and stearyl alcohol, alone or in mixture; the fat alcohols of oxethylated lanolin or oxethylated lanolin; polyglyceroyl ether of saturated or unsaturated fat alcohols and alkyl phenols containing 8 to 30 carbon atoms in the alkyl radical and 1 to 10 glyceryl units in the molecule; fatty acid alkanol amides and oxethylated sorbitan fatty esters;

(c) the cationic surface-active agents, as for example, the dilauryl dimethyl ammonium chloride, the chlorides or bromides of alkyl dimethyl benzyl ammonium, the alkyl trimethyl ammonium salts, for example, cetyl trimethyl ammonium chloride or bromide tetradecyl trimethyl ammonium chloride or bromide, the alkyl dimethyl hydroxy-ethyl ammonium chlorides or bromides, the dialkyl dimethyl ammonium chlorides or bromides, alkyl pyridinium salts, for example, lauryl or cetyl pyridinium chloride, the alkyl amide ethyl dimethyl, trimethyl ammonium ether sulphates, imidazoline derivatives, compounds having a cationic character such as amine oxides, for example, alkyl dimethyl amine oxides or alkyl aminoethyl dimethyl amine oxides;

(d) the amphoteric or zwitter-ionic surface-active agents, as for example, the carboxyl derivatives of imidazole, the N-alkyl betaines, the N-alkyl aminobetaines, the N-alkyl sulphobetaines, the N-alkyl aminopropionates, the alkyl dimethyl ammonium acetates, the $C_{12}$ to $C_{18}$-alkyl dimethyl carboxy-methyl ammonium salts and the fatty acid alkyl amido betaines, for example, dimethyl carboxy-methylene propylene amido stearate betaine.

Of course, apart from the above-mentioned ingredients the composition according to the present invention can also contain conventional additives, for example, perfume oils in an amount of approximately 0.5 to 5.0% by weight, opacifiers, as for example, ethylene glycol distearate in an amount of approximately 0.5 to 5.0% by weight, pearly luster agents, as for example, a mixture of fatty acid monoalkylol amide and ethylene glycol distearate in an amount of approximately 1.0 to 10.0% by weight, thickeners, as for example, coconut fatty acid diethyanol amide, in an amount of approximately 0.5 to 10.0% by weight, diluents, as for example, 1,2-propylene glycol or ethoxylated sorbitan monolaurate, in an amount of approximately 0.5 to 5.0% by weight, buffer substances, as for example, sodium citrate or sodium phosphate, in an amount of approximately 0.1 to 1.0% by weight, dissolving intermediaries, as for example, ethoxylated, when required, hydrogenated castor oil, in an amount of approximately 0.1 to 1.0% by weight, and dyes, as for example, fluroescin sodium salt in an amount of approximately 0.1 to 1.0% by weight, as well as hair- and skin-care additives, as for example, fatty esters, fat alcohols, fatty acid glycerides, ethoxylated propoxylated saturated fat alcohols, cellulose derivatives, cationic cellulose derivatives, chitosen, cationic chitin derivatives, lanolin derivatives, cholesterol and pantothenic acid in an amount of approximately 0.1 to 10% by weight, and also physiologically compatible inorganic salts, as for example, sodium chloride as well as moisture keeping agents, sunscreen chemicals, anti-oxidants, complexing agents and active antidruff components.

Further conventional ingredients that are known for these agents and can be contained in the novel composition are described, for example, by H. Janistyn in "Handbuch der Kosmetika und Riechstoffe", 3$^{rd}$ Volume (1973), Page 228 to 284 and 442 to 462, by K. Schrader in "Grundlagen une Rezepturen der Kosmetika" (1979), Page 375 to 401 and 445 to 455 and by G. A. Nowak in "Die kosmetischen Präparate" (1984) Page 452 to 512.

The following examples will describe the present invention in greater detail without restricting it thereto.

EXAMPLES

Hair- and Body-Cleaning Compositions

Example 1

Hair Cleaning Composition

| | |
|---|---|
| 0.15 g | of sodium formate |
| 0.20 g | of benzoic acid |
| 16.00 g | of lauryl alcohol diglycol ether sulphate sodium salt (70% aqueous gel) |
| 0.25 g | of cationic cellulose derivative (for example, Polymer JR ® - 400 of the firm of Union Carbide Corp.) |
| 0.30 g | of perfume oil |
| 3.80 g | of sodium chloride |
| 79.30 g | of fully desalted water |
| 100.00 g | |

The above hair-cleaning composition, whose pH value is adjusted with citric acid to 5–5.8, is very well preserved and outstandingly compatible.

Example 2

Hair-Cleaning Composition

| | |
|---|---|
| 0.15 g | of sodium formate |
| 0.25 g | of sodium benzoate |
| 16.00 g | of lauryl acohol diglycol ether sulphate, sodium salt (70% aqueous gel) |
| 0.25 g | of cationic cellulose derivative (for example, polymer JR ® - 400 of the firm of Union Carbide Corp.) |
| 0.30 g | of perfume oil |
| 3.80 g | of sodium chloride |
| 79.25 g | of fully desalted water |
| 100.00 g | |

The above hair-cleaning composition, whose pH value is adjusted with phosphoric acid to 5.0–5.8, is very well preserved and well compatible.

Example 3

Mild Body-Cleaning Composition

| | |
|---|---|
| 0.15 g | of sodium formate |
| 0.20 g | of benzoic acid |
| 20.00 g | of lauryl alcohol diglycol ether sulphate (70% aqueous gel) |
| 5.00 g | of fatty acid amidoalkyl betaine |
| 2.00 g | of coconut fatty acid diethanol amide |
| 0.50 g | of perfume oil |
| 4.00 g | of sodium chloride |
| 68.15 g | of fully desalted water |
| 100.00 g | |

The above body-cleaning composition, whose pH value is adjusted with citric acid to 5.0–5.8, is very well preserved and outstandingly compatible.

Unless otherwise stated, all the data in the present application relate to percent by weight.

It will be understood that each of the elements described above, or two or more together, may also find a useful application in other types of compositions differing from those described above.

While our invention has been illustrated and described as embodied in a hair- and body-cleaning composition, it is not intended to be limited to the details shown, since various modifications and structural changes may be made without departing in any way from the spirit of our present invention.

Without further analysis, the foregoing will so fully reveal the gist of our present invention that others can, by applying current knowledge, readily adapt it for various applications without omitting features that, from the standpoint of prior art, fairly constitute essential characteristics of the generic or specific aspects of our present invention.

What is claimed as new and desired to be protected by Letters Patent is set forth in the appended claims:

1. An aqueous hair- and body-cleaning composition having physiological and dermatological compatibility properties as well as a germ-inhibiting effect, said composition containing 3 to 50 percent by weight of a member selected from the group consisting of a surfactant and a surfactant mixture, from 0.01 to 2.0 percent by weight of a salt of formic acid selected from the group consisting of sodium formate, ammonium formate, potassium formate and magnesium formate, from 0.05 to 2.0 percent by weight of an element selected from the group consisting of benzoic acid and salts of said benzoic acid, said salts of said benzoic acid being selected from the group consisting of ammonium benzoate and alkali metal benzoates, and from 0.1 to 1.5 percent by weight of a member of the group consisting of phosphoric acid and aliphatic organic acids containing from 2 to 6 carbon atoms and being free of amino and halogen substituents.

2. A composition according to claim 1, wherein said salt of said formic acid comprises sodium formate.

3. A composition according to claim 1, which contains 0.1 to 1.0 percent by weight of said salt of said formic acid.

4. A composition according to claim 1, which contains 0.1 to 1.0 percent by weight of said element selected from said group consisting of said benzoic acid and said salt of said benzoic acid.

5. A composition according to claim 1, in which said element selected from said group consisting of said benzoic acid and said salt of said benzoic acid comprises an ammonium benzoate.

6. A composition according to claim 1, which has a pH value of from 2.0 to 7.0.

7. A composition according to claim 1, which has a pH value of from 4.8 to 5.8.

8. A composition according to claim 1, in which said aliphatic organic acid is an element selected from the group consisting of citric acid, tartaric acid, lactic acid, adipic acid, maleic acid, glyoxylic acid and gluconic acid.

9. A composition according to claim 1, in which said aliphatic organic acid comprises citric acid.

10. A composition according to claim 1, containing 0.25 to 0.5 percent by weight of said member of said group consisting of said phosphoric acid and said aliphatic organic acids.

11. A composition according to claim 1, wherein said surfactant is anionic.

12. A composition according to claim 1, containing 10 to 25 percent by weight of said surfactant.

13. A composition according to claim 1, wherein said aliphatic organic acid is maleic acid.

14. A composition according to claim 1, in which said element selected from said group consisting of said benzoic acid and said salt of said benzoic acid comprises an alkali metal benzoate.

15. A composition according to claim 14 wherein said alkali metal benzoate comprises sodium benzoate.

16. An aqueous hair- and body-cleaning composition having physiological and dermatological compatibility properties as well as a germ-inhibiting effect, said composition containing 3 to 50 percent by weight of a member selected from the group consisting of a surfactant and a surfactant mixture, from 0.01 to 2.0 percent by weight of a salt of formic acid, from 0.05 to 2.0 percent by weight of an element selected from the group consisting of benzoic acid and salts of said benzoic acid and from 0.1 to 1.5 percent by weight of a member of the group consisting of inorganic acids and aliphatic organic acids containing from 2 to 6 carbon atoms and being free of amino and halogen substituents.

17. A composition according to claim 16, wherein said salt of said benzoic acid comprises sodium benzoate.

18. A composition according to claim 16, wherein said inorganic acid comprises phosphoric acid.

19. A composition according to claim 16, wherein said aliphatic organic acid comprises citric acid.

20. A composition according to claim 16, wherein said aliphatic organic acid comprises maleic acid.

21. A method of preserving a hair- and body-cleaning composition which comprises adding thereto a germ-inhibiting composition with physiological and dermatological compatibility properties, said composition containing from 0.01 to 2.0 percent by weight of a salt of formic acid selected from the group consisting of sodium formate, ammonium formate, potassium formate and magnesium formate, from 0.05 to 2.0 percent by weight of an element selected from the group consisting of benzoic acid and salts of said benzoic acid, said salts of said benzoic acid being selected from the group consisting of ammonium benzoate and alkali metal benzoates, and from 0.1 to 1.5 percent by weight of a member of the group consisting of phosphoric acid and aliphatic organic acids containing from 2 to 6 carbon atoms and being free of amino and halogen substituents.

22. A method of preserving a hair- and body-cleaning composition which comprises adding thereto a germ-inhibiting composition with physiological and dermatological compatibility properties, said composition containing from 0.01 to 2.0 percent by weight of a salt of formic acid, from 0.05 to 2.0 percent by weight of an element selected from the group consisting of benzoic acid and salts of said benzoic acid and from 0.1 to 1.5 percent by weight of a member of the group consisting of inorganic acids and aliphatic organic acids containing from 2 to 6 carbon atoms free of amino and halogen substituents.

* * * * *

UNITED STATES PATENT AND TRADEMARK OFFICE
CERTIFICATE OF CORRECTION

PATENT NO. : 4 971 784

DATED : November 20, 1990

INVENTOR(S) : Hans Hölzel, Eugen Konrad and Horst Schwarz

It is certified that error appears in the above-identified patent and that said Letters Patent is hereby corrected as shown below:

ON TITLE PAGE: [75] The address of Horst Schwarz should read --Seeheim--

Signed and Sealed this

Fourth Day of August, 1992

Attest:

DOUGLAS B. COMER

Attesting Officer     Acting Commissioner of Patents and Trademarks